US006763084B2

(12) United States Patent
Boehm et al.

(10) Patent No.: US 6,763,084 B2
(45) Date of Patent: Jul. 13, 2004

(54) METHOD FOR OPERATING AN IMAGE SYSTEM OF AN IMAGING MEDICAL EXAMINATION DEVICE AND MEDICAL EXAMINATION DEVICE

(75) Inventors: Stefan Boehm, Zirndorf (DE); Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/990,346

(22) Filed: Nov. 23, 2001

(65) Prior Publication Data

US 2002/0065611 A1 May 30, 2002

(30) Foreign Application Priority Data

Nov. 24, 2000 (DE) .......................................... 100 58 388
May 11, 2001 (DE) .......................................... 101 22 876

(51) Int. Cl.[7] ............................................. G01N 23/24
(52) U.S. Cl. ........................... 378/62; 382/275; 382/128
(58) Field of Search ........................ 378/62, 98.8, 98.2, 378/98.3, 207; 250/370.09, 370.08, 370.01; 382/132, 128, 275, 149, 272; 348/246; 358/213.17

(56) References Cited

U.S. PATENT DOCUMENTS

| 4,701,784 A | * | 10/1987 | Matsuoka et al. .......... 348/247 |
| 5,144,446 A | * | 9/1992 | Sudo et al. ............ 358/213.11 |
| 5,436,659 A | * | 7/1995 | Vincent ...................... 348/246 |
| 5,712,890 A | * | 1/1998 | Spivey et al. ................. 378/37 |
| 5,854,655 A | * | 12/1998 | Watanabe et al. ........... 348/247 |
| 5,886,353 A | * | 3/1999 | Spivey et al. .......... 250/370.09 |
| 6,002,433 A | * | 12/1999 | Watanabe et al. ........... 348/246 |
| 6,381,357 B1 | * | 4/2002 | Tan et al. .................... 382/141 |
| 6,418,241 B1 | * | 7/2002 | Schreiner ..................... 382/263 |
| 6,526,366 B1 | * | 2/2003 | Dunton ....................... 702/116 |
| 6,529,618 B1 | * | 3/2003 | Ohara et al. ................. 382/132 |
| 6,529,622 B1 | * | 3/2003 | Pourjavid .............. 250/370.09 |
| 6,614,946 B1 | * | 9/2003 | Edgar et al. ................. 382/275 |
| 2002/0196354 A1 | * | 12/2002 | Chang et al. ............... 348/246 |
| 2003/0063202 A1 | * | 4/2003 | Toyoda et al. .............. 348/246 |

FOREIGN PATENT DOCUMENTS

| DE | 40 42 588 C2 | 7/1991 |
| DE | 195 25 274 A1 | 1/1997 |
| DE | 195 27 148 C1 | 1/1997 |
| DE | 195 27 179 C1 | 1/1997 |
| EP | 0 687 106 A1 | 12/1995 |

* cited by examiner

Primary Examiner—David V. Bruce
Assistant Examiner—Irakli Ikiknadze
(74) Attorney, Agent, or Firm—Young & Thompson

(57) ABSTRACT

In a method for operating an imaging medical examination device (1), an event of the undisturbed operation of the medical examination device (1) automatically triggers a defect determination (63) for determining a defective pixel possibly present in the image. The event is derived for example from a switch-on process, a calibration process and/or an examination process. Preferably, after the defect determination (63), a correction process (67) is automatically triggered if a defective pixel was detected. A medical examination device (1) has a detection device (31) for automatically determining a defective pixel possibly present in the image, in which case the detection device (31) can be activated by an event of the undisturbed operation of the medical examination device. A correction device (41) for automatically eliminating a defective pixel that has possibly been detected is preferably present.

29 Claims, 3 Drawing Sheets

METHOD FOR OPERATING AN IMAGE SYSTEM OF AN IMAGING MEDICAL EXAMINATION DEVICE AND MEDICAL EXAMINATION DEVICE

BACKGROUND OF THE INVENTION

The invention relates to a method for operating an image system of an imaging medical examination device, the image system having a reception unit for receiving a plurality of signals arising at different locations, and a display unit for the imaging representation of pixels, the pixels each being assigned at least one signal. The invention additionally relates to an imaging medical examination device having an image system, the image system having a reception unit for receiving a plurality of signals arising at different locations, and a display unit for the imaging representation of pixels, the pixels each being assigned at least one signal.

In medical X-ray technology use is made of digital imaging systems having a reception unit with a digital image converter—instead of an analog image converter. Such a digital image converter acquires an image comprising a plurality of pixels. An individual pixel can be generated e.g. by the signal of an individual element of a photodiode array, of a CCD image converter or an amorphous silicon detector (a:Si detector). The individual elements receive light signals arising at different locations and image them on a display unit in an imaging fashion.

Image converters of this type can be affected by pixel failures caused e.g. by the failure of an individual converter element. There may also be pixel failures in groups (so-called clusters), which lead to the failure of entire lines or columns and are caused for example by interruptions in the address lines.

The failure of one or more pixels or measurement channels can lead to image artifacts of greater or lesser severity, which become visible for example as black rings in a computer tomograph image. If every image converter affected by such an artifact were discarded from the series during the production of a digital image system, this would lead to a high reject rate. On the other hand, however, given the multiplicity of pixels present, it is not necessary for the signal of every individual measurement channel to reach the imaging stage. In order to decrease the rejection of detectors, it is known, therefore, for example from DE 195 27 179 C1 or from DE 195 27 148 C1, to correct a defective pixel. For this purpose, the procedure is performed in two steps: firstly a defect determination takes place, which yields information about which pixels are defective and which are good. When this information is present, the defective pixels can be corrected in a second step. The correction can be achieved for example by replacing the defective pixels by linear interpolation of adjacent pixels. For the correction of column or line defects, DE 195 27 179 C1 discloses proceeding separately according to line defects in a first correction step and according to column defects in a second correction step.

A correction circuit—based on an interpolation method—for correcting defective pixels in an image system or a CCD apparatus is also disclosed in EP 0 687 106 A1.

SUMMARY OF THE INVENTION

Proceeding from an image system with a potentially defective pixel, the invention is based on the object of specifying a method for operating such an image system in an imaging medical examination device which improves the reliability of the operation of the image system. An imaging medical examination device having an image system is also intended to be specified for the same purpose.

The first-mentioned object is achieved, relative to a method of the type mentioned in the introduction, by virtue of the fact that an event of the undisturbed operation of the medical examination device automatically triggers a defect determination for determining a defective pixel possibly present in the image.

The defect determination can be performed as it were on line during use and not just once after the production of the digital image sensor or during the calibration thereof. This makes it possible firstly for imminent defects already to be identified at a point in time at which the image is not yet severely disturbed. Secondly, it is thus possible to effect continuous correction of newly occurring defects, so that even over a long period of operation, the quality of the images recorded by the image sensor having an increasing number of defects is not impaired or is virtually unimpaired.

In particular, an event that occurs anyway during operation is used or a triggering event is generated during the undisturbed operation.

In this case, the invention is based on the insight that in image systems of future medical examination devices, defective pixels will have to be reckoned with to an increasing extent, since the number of detector channels will rise. It will increasingly happen that such image or channel failures will not occur until during clinical operation and interrupt the latter or at least cause massive disruption thereto. Although occasionally the defects may arise as early as during the production of the digital image converter, there is nonetheless the risk that further defects or indeed the first manifestation of defects will occur during the use and operation of the digital image converter, that is to say e.g. during clinical use, and interrupt the latter or at least cause massive disruption thereto. In the case of the method according to the invention, such defects and, consequently, an operational disruption are counteracted since the defect determination is triggered automatically. This means that it is possible, in particular, for an imminent defect already to be detected at a point in time at which the image is not yet severely disturbed, in order to initiate suitable countermeasures before the occurrence of a later severe disturbance. The method additionally has the advantage that separate intervention by an operator is not necessary to trigger the defect determination. Rather, the defect determination can take place without the action and even without the knowledge of an operator.

According to a preferred embodiment, the triggering event is derived from an operating process which does not serve for the defect determination, in particular from an operator's control process which does not serve for the defect determination.

Preferably, the triggering event is derived from a switch-on process performed on the medical examination device. By way of example, a defect determination sequence or a defect determination algorithm is automatically triggered when the medical examination device is switched on.

It is likewise preferred for the triggering event to be derived from a calibration process performed on the medical examination device. Such a calibration process is carried out e.g. when the examination device is switched on or during the operation of said examination device by an operator, e.g. by a doctor. During this calibration process, the image channels or pixels are calibrated individually and immediately examined with regard to a defect during this opportunity.

Preferably, the triggering event is generated at a defined point in time before, during or after an image acquisition procedure, in particular before, during or after a patient examination or a scan.

The triggering event can also be generated by a counting process. In particular, the counting process counts a process which is repeated during operation of the medical examination device, in particular a switch-on process, a calibration process and/or examination process. A trigger signal as the triggering event is triggered for example whenever the counting process has continued counting by a constant interval. This affords the advantage that a defect determination is automatically triggered whenever the image system has been exposed to a high load and, accordingly, it is with increased probability that the occurrence of defects is to be reckoned with.

It is likewise preferred for the triggering event to be generated by a time measuring process. For this purpose, a corresponding trigger signal can be derived for example from a clock generator or a timer of a computer which controls the examination device. By way of example, a trigger signal or trigger event is generated at fixed time intervals, for example hourly.

According to an especially preferred refinement, after the defect determination, a correction process is automatically triggered if a defective pixel was detected. As a result, outage times of the examination device in clinical operation are avoided to the greatest possible extent. Image artifacts become visible only to a very small extent or only sporadically.

Preferably, during the correction process, the assignment of the defective pixel to its signal is canceled and, instead of this, the pixel is assigned one or more signals of one or more other pixels. By way of example, interpolation from the signals of adjacent pixels takes place.

The above-described correction process by newly assigning one or more signals of one or more other pixels to a defective pixel leads to complete elimination of an image artifact. Such a correction process is carried out as sole correction measure in particular in the edge area of a computer tomograph image, since, in the edge area, the failure of the information from a single pixel does not lead to significant impairment of the meaningfulness of the image.

The automatic performance of a correction process has the advantage that the service costs for the examination device are significantly reduced since the attendance of service personnel will in many cases not be necessary.

The correction process is, in particular, an interpolation process in which interpolation is effected, for example linearly, between pixels adjacent to a defective pixel. By way of example, the correction process according to the patent claims of DE 195 27 179 C1 is employed. It is also possible to use the correction measures described in EP 0 687 106 A1, in particular as set forth therein in the claims.

The defect determination takes place, in particular, according to a method as disclosed in the patent claims of DE 195 27 148 C1.

The medical examination device is, for example, a computer tomograph, a magnetic resonance imaging scanner or a conventional X-ray apparatus, e.g. a radiography apparatus.

In one specific embodiment of the method, it is provided that in connection with the defect determination after carrying out a first correction process in which already known image defects are corrected, the corrected image is analyzed in order to determine further defects or defects that are still present, which are corrected in a second correction process. Thus, a two-stage correction takes place.

In the specific embodiment mentioned, the method according to the invention advantageously provides a two-stage correction of an image currently being recorded, or of a chronologically previously recorded image loaded from a memory. First of all, in a first correction process, a first correction of the image or of the image signals is effected in order to correct already known defects which were determined e.g. as early as after the production of the reception unit in the context of serviceability tests. After this correction process, an image is present which has been corrected for the first time and is already largely free of defects on account of the correction. In order then to identify new defects, the already corrected image is subsequently analyzed. Depending on whether or not further defects are then identified, the image is either corrected in a second correction process in order to eliminate the new defects, if such have been detected. If no further defects are present, then the image can be processed further and output.

What is effected here, then, is firstly a correction of the defects known as it were "off line" and, in addition, a correction of the defects ascertained "on line", on account of the defect analysis, performed according to the invention, of the image currently being recorded. The correction is thus effected with regard to the defects that are actually present in the image, and not just with regard to the already known defects that were indeed determined earlier and, if appropriate, may only constitute a portion of the overall defects.

The image itself can be filtered after the first correction process, after which the filtered image is first analyzed, in which case e.g. a median filter or a high-pass filter can be used as the filter. The defect-free image areas are filtered out in the context of this filtering, with the result that only image areas that are possibly still affected by defects are visible in the filtered image on which the analysis is based.

According to the invention, in the context of the analysis, the pixel-related signals may then be compared with one or more threshold values. A defect may be identified in the context of this analysis e.g. from the fact that the signal falls below a threshold value or, alternatively, that the signal or the signal noise exceeds or falls below a specific threshold value. A defect can also be identified using already filtered signals in the manner described. In a development of the invention, this analysis result may then be used to generate a new defect map, which describes the detected defect or defects that is or are new or still present, and which is used to effect the correction in the second correction process. In this case—like the first correction previously—the correction can be effected by means of any known correction method, e.g. by means of the correction methods already described in the documents DE 195 27 179 C1 or DE 195 27 148 C1 mentioned in the introduction.

In this case, in the context of the first correction process, the image may be corrected using an old defect map, which describes already known defects. This old defect map is used as a basis for the first correction process; it specifies the position of the already known defects, as were determined e.g. after the production of the reception unit or in the course of earlier calibration, thereby enabling a targeted defect correction in the context of the first correction process.

Since the newly detected defects are normally permanent defects which would likewise occur again in subsequently recorded images, it has proved to be particularly expedient if the old defect map is updated using the new defect map. In other words, the newly determined defects are concurrently included in the old defect map, and the latter is thus adapted to the given defect situation and updated, with the result that, in the context of the first correction process of a subsequently recorded image, both the new defects already known at the time and the new defects determined in the last detection and correction step are immediately corrected. The old defect map is thus continuously adapted to the actual defect state.

In this case, the updating can be effected only when one or more defects that are newly present or still present are detected. This advantageously avoids the situation in which a step of updating the old defect map takes place after each new defect determination even when no new defects have been determined.

Finally, it may be provided that a flat-fielding correction of the image is effected in the context of the first correction process. In the context of this known flat-fielding correction, firstly the recorded image is corrected using an offset image, by means of which the originally provided offset of the digital reception unit is corrected. Furthermore, a correction is effected using a gain image, which takes account of the different gain factors of the individual pixels. This flat-fielding correction is intrinsically known per se and need not be discussed in any further detail.

Moreover, the method is configured in a particularly preferred manner in that after the defect determination, a message is automatically sent via a data link to a service device if a defective pixel was detected. This affords the advantage that the service device is continuously informed about defects that occur on the examination device. It can then decide remotely, for example, whether a correction process that may already have been triggered automatically suffices to eliminate the defective pixel, or whether further-reaching measures should be initiated, e.g. replacing the reception unit.

When the defect determination is carried out, a pixel is detected as defective preferably by virtue of the fact that the assigned signal falls below a minimum value and/or the noise in the assigned signal exceeds a maximum value. The determination of the noise, in particular, enables imminent defects to be identified in good time.

The defect determination can also be carried out on a stored image. This is advantageous in particular if the defect determination is triggered by an event at the instant of whose occurrence no image data are regularly present, such as e.g. if a trigger signal is generated at fixed time intervals.

The apparatus-related object is achieved, relative to the medical examination device mentioned in the introduction, by means of a detection device for automatically determining a defective pixel possibly present in the image, in which case the detection device can be activated by an event of the undisturbed operation of the medical examination device.

Such a medical examination device is particularly suitable for carrying out the method according to the invention. When the detection device is activated, the defect determination can be triggered in said detection device.

The advantages and configurations mentioned with regard to the method apply analogously to the medical examination device according to the invention.

Preferably, the detection device can detect a pixel as defective if the assigned signal falls below a minimum value and/or if the noise in the assigned signal exceeds a maximum value.

According to a particularly preferred refinement, the examination device has a correction device for automatically eliminating a defective pixel that has possibly been detected, in which case the correction device is connected to the detection device and can be activated by the latter if a defective pixel is detected.

Such a preferred examination device is distinguished for example by the fact that the detection device is designed for analysis of the image that has been corrected by means of the correction device a first time with regard to already known defects, for the purpose of determining defects that are new or still present, and the correction device is designed for renewed correction of the corrected image with regard to the defect or defects that is or are new or still present.

In this case, the detection device has a filter for filtering the image after the first correction process and an analysis means for determining one or more defects that is or are new or still present, the filter expediently being a median filter or a high-pass filter.

The analysis means itself may be designed for comparing the pixel-related signals with one or more threshold values for the purpose of determining a defect. Furthermore, the analysis means or the detection device may be designed for generating a new defect map, which describes the detected defect or defects that is or are new or still present, and the correction device may be designed for correcting the image in the second correction process using the new defect map. Finally, the correction device may be designed for correcting the image using an old defect map, which describes already known defects, in the context of the first correction process.

Furthermore, it is expedient if the detection device or the correction device is designed for updating the old defect map using the new defect map. In this case, the respective defect maps may be stored either in the detection device or the correction device, that device where the defect maps are stored expediently carrying out the corresponding updating.

Finally, the correction device may be designed for carrying out a flat-fielding correction of the image in the context of the first correction process.

It is additionally preferred for the detection device to have a data interface for sending a message to a service device, in which case the message can be sent automatically by the detection device if a defective pixel is detected.

The detection device may also be connected to an image memory, from which it is possible to retrieve an image which was generated by the image system at an earlier point in time.

BRIEF DESCRIPTION OF THE DRAWINGS

Exemplary embodiments of an examination device and of a method according to the invention are explained in more detail below with reference to FIGS. 1 to 3, in which.

DESCRIPTION OF THE PREFERRED ENBODIMENT

Figure 1:
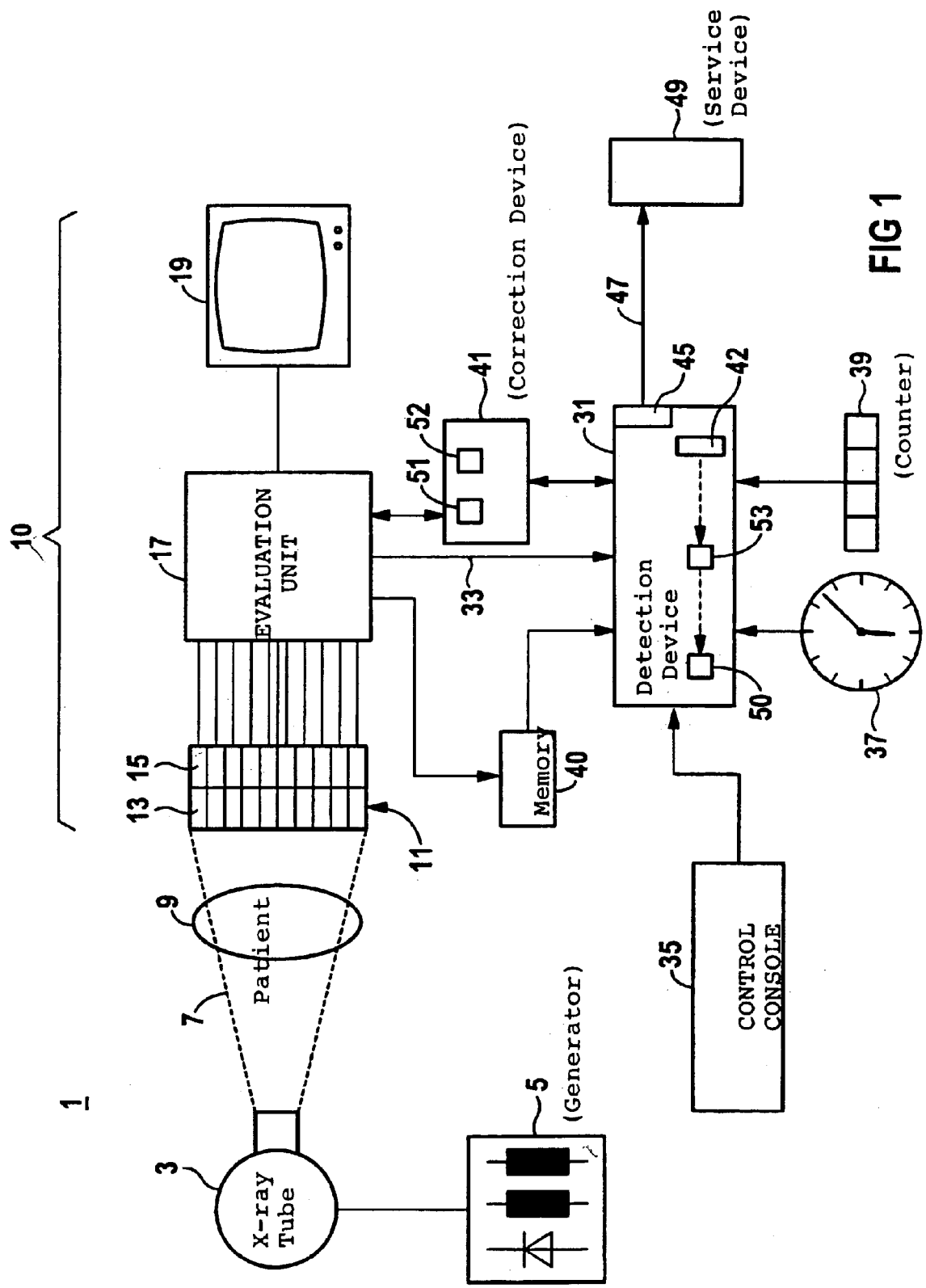
FIG. 1 shows a medical examination device according to the invention in a diagrammatic overview.

FIG. 1 shows a medical examination device designated in its entirety by the reference numeral 1, said device comprising an X-ray tube 3 fed by a high-voltage generator 5. An X-ray beam 7 emitted by the X-ray tube 3 penetrates through a patient 9 and passes to a digital image system 10 of the examination device 1 in accordance with the location-dependent transparency of the patient 9.

The image system 10 has a reception unit 11 composed of a scintillator matrix 13 and a photodiode array 15. In the scintillator matrix 13, wave conversion from invisible X-ray radiation into radiation detectable for semiconductor diodes takes place. Each pixel of the scintillator matrix 13 is assigned an element of the photodiode array 15, with the result that the light signals arising at different locations in accordance with the location-dependent transparency of the patient 9 are converted into electronic signals.

The individual channels of the reception unit 11 are fed to an evaluation unit 17, which, for its part, is connected to a display unit 19, e.g. a screen. In the evaluation unit 17, the signals of the individual image channels are conditioned and converted into a video signal.

The examination device 1 additionally has a detection device 31 for automatically determining a defective pixel possibly present in the image of the display unit 19. The detection device 31 is connected to the evaluation unit 17 via a data line 33 and receives, via said data line 33, information about the signals of the individual pixels or channels.

The detection device 31 can be triggered or activated by different events:

a) by one or more control processes performed by an operator which are defined in advance and are performed on a control console 35, e.g. by a switch-on process, by a calibration process or by an examination process or an individual image recording (see e.g. reference symbol 75 in FIG. 3),
b) by a time-controlled signal from a clock 37,
c) by a counter-controlled signal from a counter 39 which counts the number of patient examinations performed.

The detection device 31 can be activated by one or more of these trigger processes a) to c). In the case of activation of the detection device 31, the image data that are currently available via the data line 33, or the image data that were stored in an image memory 40 at an earlier point in time, are automatically analyzed with regard to defective pixels. For this purpose, the detection device 31 has an analysis means 42, which is designed e.g. for comparing the individual pixel-related image signals of the image to be analyzed with suitable threshold values.

The detection device 31 is connected to a correction device 41, which, for its part, acts on the evaluation unit 17. In the case where a defective pixel has been determined by the detection device 31, a correction process is automatically initiated in the correction device 41, the defective pixel being eliminated by means of said correction process. By way of example, a correction procedure is implemented in the correction device 41, which correction procedure cancels the assignment of the defective pixel to its previous signal, and, after the execution of said correction procedure, the pixel is instead assigned one or more signals of one or more adjacent pixels. By way of example, interpolation is effected between adjacent pixels.

In addition or as an alternative to the triggering of the correction process, a message is automatically generated by the detection device 31 when a defective pixel appears. For this case, the detection device 31 has a data interface 45 from which there leads a data link 47 to a service device 49. The message is sent automatically by the detection device 31.

In addition to or besides an interpolation method, low-pass filtering can also be started by the correction device 41.

In the exemplary embodiment shown, the examination device 1 is designed in such a way that the correction can also be effected in two steps. For this purpose, an old defect map 50 is stored in the detection device 31. Already known defects of the reception unit 11, which lead to image artifacts, are described and defined in said old defect map 50. The correction device 41 is then designed in such a way that, in a first correction step, the raw image data supplied to the correction device 41 by the detection device 31 are corrected a first time by means of or on the basis of the old defect map 50, in order to correct the already known defects prior to the actual analysis of the image with regard to new defects. This correction using the old defect map 50 precedes a flat-fielding correction using an offset image 51 and a gain image 52, which are stored in the correction device 41 in the example shown.

The image corrected in this way in a first correction process is subsequently passed to the detection device 31, where it is analyzed by the analysis means 42. The analysis means 42 generates a new defect map 53, provided that new defects are detected. Using this new defect map 53, the image data that have already been corrected in the first correction process are then corrected a further time in the correction device 41 for the purpose of eliminating the new defects. After this second correction process has been carried out, the corrected image data are passed from the correction device 41 to the evaluation unit 17 again and can then be displayed; of course, it is also conceivable for the corrected image data to be written to the memory 40, etc. As is furthermore illustrated in FIG. 1, the old defect map 50 is subsequently updated using the new defect map 53, with the result that, during a subsequent image correction of an image recorded later, the totality of all the defects then known, which is acquired in the preceding processing step, is corrected.

Figure 2:
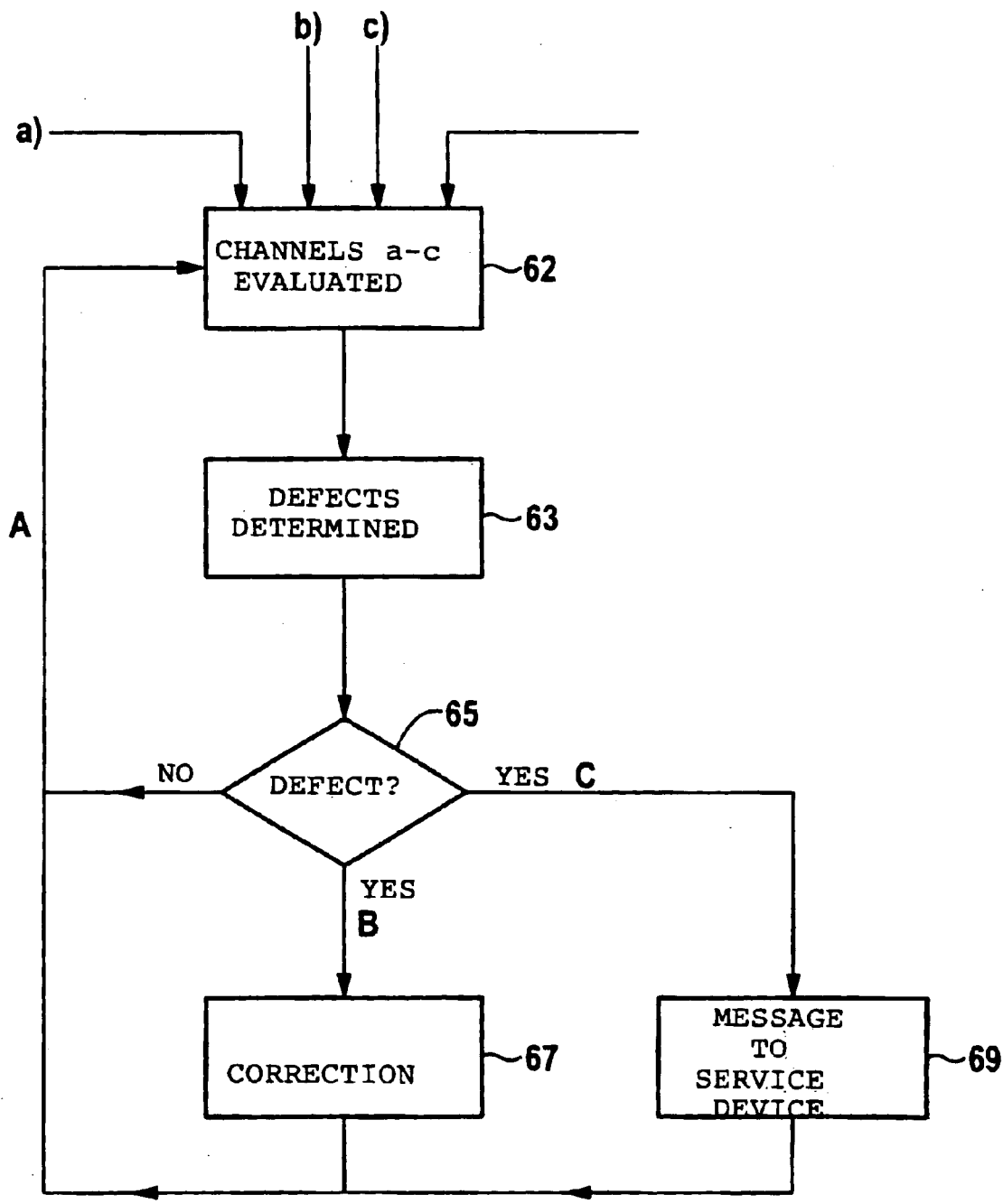
FIG. 2 shows a flow diagram of a method according to the invention in a first exemplary embodiment.

FIG. 2 shows a first example of a flow diagram of a method according to the invention in simplified form. First of all, an event determination 62 takes place. Various event channels a, b and c are evaluated for this purpose. What are involved in this case are events as occur in the undisturbed operation of the examination device 1 and have been enumerated for example in connection with the description of FIG. 1.

After an event has been determined and identified as such, a defect determination 63 automatically takes place, in other words all the pixels present are checked with regard to their functionality. That is done by checking each channel with regard to a minimum signal strength.

Afterward, a decision 65 is taken in a manner dependent on the result of the defect determination 63. If no defect was determined, the procedure returns (A) to the state of the event determination 62 and again waits for an event. If a defect was determined, a correction process 67 ("channel patch") automatically takes place (B) and/or a message 69 is sent (C) to the service device 49. Afterward, in these cases, (B, C), too, the procedure returns to the waiting state of the event determination 62.

The remote service personnel determine whether—for example in the case of a severe image artifact in the center of the image or in the case of a bone soft-part transmission in an unfavorable projection direction during computer tomography—the reception unit should be replaced entirely or modularly.

Figure 3:
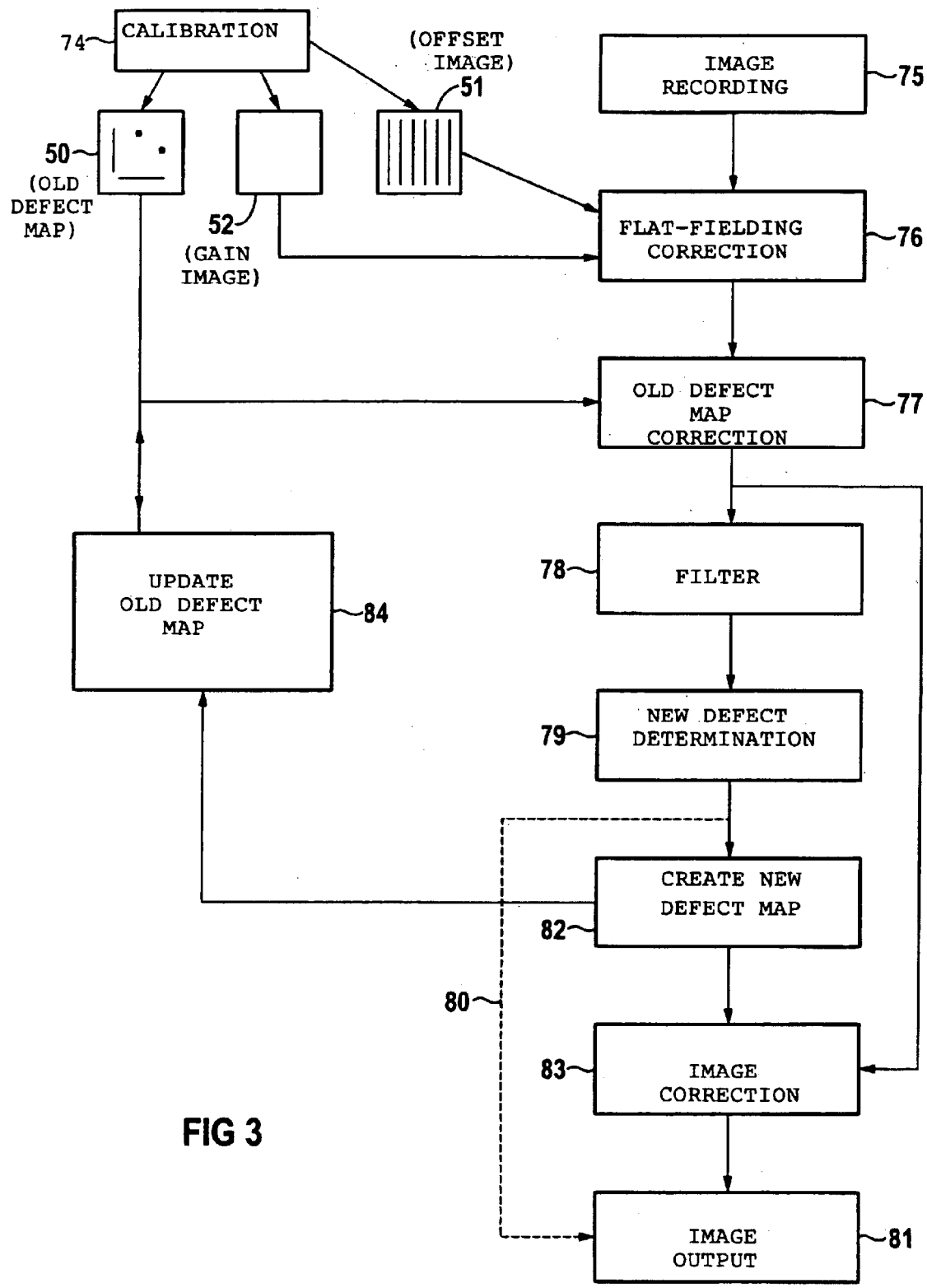
FIG. 3 shows a flow diagram of a method according to the invention in a second exemplary embodiment.

FIG. 3 shows a flow diagram of a second exemplary embodiment of the method according to the invention, to be precise with correction in two correction steps.

First of all, calibration ensues in a step 74. Said calibration is carried out e.g. at predetermined time intervals, e.g. every three months or every six months. In the context of this calibration, firstly an old defect map 50, already described with regard to FIG. 1, is determined by means of known defect determination methods. This old defect map 50 determines the position of detected defects in a recorded calibration image. In the example shown, a line defect, a column defect and also two cluster defects are illustrated by way of example.

Furthermore, an offset image 51 and also a gain image 52 are determined in the context of the calibration. These correction means, namely the old defect map 50, the offset image 51 and the gain image 52, are stored in the detection device 31 and the correction device 41, respectively.

If an image recording 75 is then effected at an arbitrary point in time, first of all a flat-fielding correction is carried out in step 76. In the context of said flat-fielding correction, the raw image data obtained in the image recording 75 are corrected using the offset image 51 and the gain image 52. An old defect map correction is subsequently effected using the old defect map 50 in step 77.

The image that has been corrected in this way in the first correction process is then filtered in step 78 e.g. by means of a median or high-pass filter, after which the filtered image, by means of step 79, is subjected to an analysis for the purpose of new defect determination by the analysis means 42. If the new defect analysis reveals that there are no new defects, the image is immediately output 81—see the broken line 80. However, if one or more defects or defects that are still present are determined, then a new defect map is created in step 82, using which map, in step 83, the correction device 41 then once again corrects the image that was corrected using the old defect map 50 in step 77, in order also to correct these new defects that have now been detected as it were "on line" with respect to the respective recorded image. The image that has been doubly corrected in this way (or triply corrected if the flat-fielding correction is considered as a separate correction step) is subsequently output (step 81).

If a new defect map 53 is generated, then, in step 84, the old defect map 50 is updated using the new defect map 53, with the result that the then corrected or updated old defect map 50 describes the instantaneous actual defect state. If the then updated old defect map 50 is used as a basis, in a further process, for the correction of an image that is newly recorded later, the totality of defects known at this point in time are corrected automatically.

The evaluation unit 17 and/or the detection device 31 and/or the correction device 41 and/or the image memory 40 and/or the control console 35 and/or the clock 37 and/or the counter 39 may be designed as a component part of a computer system which controls the medical examination device 1 and its image system 10. Correspondingly, the defect determination 63, the decision 65 and/or the correction process 67 may be realized as a computer program for the computer. The event determination 62 then runs e.g. continuously in the background.

What is claimed is:

1. A method for operating an image system of an imaging medical examination device, the image system having a reception unit for receiving a plurality of signals arising at different locations and a display unit for an image of pixels, the pixels each being assigned at least one signal, the method comprising the steps of:
   automatically triggering, with a triggering event generated at a defined point in time after an image acquisition procedure, a defect determination for determining a defective pixel in the image and, after the defect determination, automatically triggering a correction process if a defective pixel was detected,
   wherein the defect determination and the correction process comprise the steps of carrying out a first correction in which already known defects are corrected using an old defect map, analyzing the results of the first correction process to create a new defect map that describes new defects not found in the old defect map, and carrying out a second correction in which the new defects are corrected using the new defect map.

2. The method as claimed in claim 1, wherein the triggering event is derived from an operating process which does not serve for the defect determination.

3. The method as claimed in claim 1, wherein the triggering event is generated at a defined point in time after a patient examination or a scan.

4. The method as claimed in claim 1, wherein the triggering event is generated by a counting process.

5. The method as claimed in claim 4, wherein the counting process counts a process which is repeated during operation of the medical examination device, the process being one of a switch-on process, a calibration process and an examination process.

6. The method as claimed in claim 1, wherein the triggering event is generated by a time measuring process.

7. The method as claimed in claim 1, wherein during the correction process, an assignment of a defective pixel to its signal is canceled and, instead of this, the defective pixel is assigned one or more signals of one or more other pixels.

8. The method as claimed in claim 1, further comprising the steps of filtering the image after the first correction and analyzing the filtered image.

9. The method as claimed in claim 8, wherein the filtering step includes filtering with one of a median and a high-pass filter.

10. The method as claimed in claim 8, wherein during the analysis, the pixel-related signals are compared with one or more threshold values.

11. The method as claimed in claim 1, wherein the old defect map is updated using the new defect map.

12. The method as claimed in claim 11, wherein the updating takes place only when one or more defects that are new or still present are detected.

13. The method as claimed in claim 1, wherein the first correction includes a flat-fielding correction of the image.

14. The method as claimed in claim 1, further comprising the step of automatically sending a message sent via a data link to a service device if a defective pixel was detected after the defect determination.

15. The method as claimed in claim 1, wherein a pixel is defective if its associated signal falls below a minimum value.

16. The method as claimed in claim 1, wherein a pixel is defective if noise in its associated signal exceeds a maximum value.

17. The method as claimed in claim 1, wherein the defect determination is carried out on a stored image.

18. An imaging medical examination device having an image system, the image system having a reception unit for receiving a plurality of signals arising at different locations and a display unit for an image of pixels, the pixels each being assigned at least one signal, the device comprising:
   a detection device for automatically determining a defective pixel in the image, said detection device being activated by an event of an undisturbed operation of the medical examination device; and
   a correction device for automatically eliminating a defective pixel that has been detected, said correction device being connected said detection device and is activated thereby if a defective pixel is detected, said detection device analyzing an image that has been corrected in said correction device in a first correction with regard to already known defects for the purpose of determining a defect that is new or still present, said correction device carrying a second correction of the corrected image with regard to a defect that is new or still present;

said detection device generating a new defect map that describes the detected defect that is new or still present, and said correction device corrects the image in the second correction using the new defect map, and said correction device correcting the image using an old defect map that describes already known defects in the first correction.

19. The examination device as claimed in claim 18, wherein said detection device detects a defective pixel when an associated signal falls below a minimum value.

20. The examination device as claimed in claim 18, wherein said detection device detects a defective pixel when noise in an associated signal exceeds a maximum value.

21. The examination device as claimed in claim 18, wherein said detection device comprises a filter for filtering the image after the first correction and an analysis means for determining a defect that is new or still present.

22. The examination device as claimed in claim 21, wherein said filter is one of a median filter and a high-pass filter.

23. The examination device as claimed in claim 22, wherein said analysis means compares a signal associated with a pixel with one or more threshold values to determine a defect.

24. The examination device as claimed in claim 18, wherein said detection device updates the old defect map using the new defect map.

25. The examination device as claimed in claim 18, wherein said correction device carries out a flat-fielding correction of the image in the first correction.

26. The examination device as claimed in claim 18, wherein said detection device comprises a data interface for sending a message to a service device, and wherein the message is sent automatically by said detection device if a defective pixel is detected.

27. The examination device as claimed in claim 18, wherein said detection device is connected to an image memory from which an image generated by the image system at an earlier time is retrievable.

28. A method for operating an image system of an imaging examination device, the method comprising the steps of:

providing an old defect map showing existing defective pixels;

generating an image;

first correcting the image by correcting the existing defective pixels with reference to the old defect map;

analyzing the first corrected image to find new defective pixels;

generating a new defect map showing the new defective pixels; and second correcting the analyzed image by correcting the new defective pixels with reference to the new defect map.

29. The method of claim 28, further comprising the steps of adding the new defective pixels to the old defect map to generate an updated defect map and replacing the old defect map with the updated defect map.

* * * * *